US008760299B2

(12) United States Patent
Roth

(10) Patent No.: US 8,760,299 B2
(45) Date of Patent: *Jun. 24, 2014

(54) METHODS FOR PROVIDING SECURE AND TRANSPARENT CACHED MONITORING DEVICE DATA

(76) Inventor: Michael Roth, Paradise Valley, AZ (US)

(*) Notice: Subject to any disclaimer, the term of this patent is extended or adjusted under 35 U.S.C. 154(b) by 222 days.

This patent is subject to a terminal disclaimer.

(21) Appl. No.: 13/295,907

(22) Filed: Nov. 14, 2011

(65) Prior Publication Data
US 2012/0072403 A1 Mar. 22, 2012

Related U.S. Application Data

(63) Continuation-in-part of application No. 12/390,995, filed on Feb. 23, 2009, now Pat. No. 8,059,003.

(51) Int. Cl.
G08B 23/00 (2006.01)

(52) U.S. Cl.
USPC ......... 340/576; 340/573.1; 180/272; 600/532

(58) Field of Classification Search
USPC .................. 340/576, 575, 438, 901, 988, 991, 340/573.1, 522; 701/33, 35, 300; 180/272, 180/279, 289; 280/735; 307/10.1; 600/532; 707/705, E17.005, E17.032
See application file for complete search history.

(56) References Cited

U.S. PATENT DOCUMENTS

| 5,303,575 | A * | 4/1994 | Brown et al. ................. 73/23.3 |
| 8,022,831 | B1 * | 9/2011 | Wood-Eyre .................. 340/575 |
| 8,059,003 | B2 * | 11/2011 | Roth ............................ 340/576 |
| 2003/0095046 | A1 * | 5/2003 | Borugian ..................... 340/576 |
| 2007/0024454 | A1 * | 2/2007 | Singhal ........................ 340/576 |
| 2008/0097909 | A1 * | 4/2008 | Dicks et al. ..................... 705/50 |

* cited by examiner

Primary Examiner — Anh V La
(74) Attorney, Agent, or Firm — The Noblitt Group, PLLC

(57) ABSTRACT

Generally, in accordance with various exemplary embodiments of the present invention, the present method comprises collecting data from monitoring devices, uploading the data from a monitoring device to a central database, pairing the data with secure transactional data to provide one or more secure transactional stamp(s), storing the data and the paired secure transactional stamp(s) in the central database, producing a report comprising the data and the paired transactional stamp, and providing the report to an authorized third party. Preferably, the transactional stamp comprising the name of personnel, time, and any changes made to the data collected from the monitoring device is generated and attached to the data. Further, the present invention discloses methods for transactional stamping all reviews of the monitoring device data and/or all client input data to produce a secure report, admissible under the Federal Rules of Evidence.

33 Claims, 6 Drawing Sheets

METHODS FOR PROVIDING SECURE AND TRANSPARENT CACHED MONITORING DEVICE DATA

CROSS-REFERENCES TO RELATED APPLICATIONS

This application is a continuation in part of U.S. patent application Ser. No. 12/390,995, now U.S. Pat. No. 8,059,003 titled Methods for Providing Secure and Transparent Cached Ignition Interlock Data" filed Feb. 23, 2009 and incorporates the disclosure of such application by reference.

BACKGROUND OF THE INVENTION

Vehicle operation by persons under the influence of alcohol is a well known safety hazard in the United States and throughout the world. Thousands of deaths per year in the United States are attributable to drivers operating vehicles under the influence of alcohol. To address this problem, the state of Arizona, like most states, has established laws that criminalize operation of a vehicle and other machinery with a blood alcohol concentration ("BAC") greater than a preset value (e.g., 0.08% BAC).

Once a person has received a citation for driving under the influence of alcohol, and depending on the outcome of their court case, they may be required to submit to test via a monitoring device to prove that they are not drinking. These tests may be required to be performed in the home, the car, and even randomly during the day. The monitoring devices come in many forms and are commercially available from a number of companies.

One such monitoring device is commonly known as the breath alcohol ignition interlock devices ("BIID" or "IID") and/or systems. These IIDs have been developed to be directly connected to a vehicle's ignition system and are designed to prevent automobiles and other machinery from being operated by inebriated individuals. To reduce the rate of recidivism of driving under the influence, the state of Arizona and other states require the installation of an IID in the vehicle and other machinery of individuals convicted of driving under the influence of alcohol.

IIDs may comprise semiconductor sensors, commonly referred to as a Taguchi cell, infrared absorption sensing systems, and/or fuel cells to sense and quantify the amount of alcohol in a driver's breath. Most modern IIDs use an ethanol-specific fuel cell for a sensor. See U.S. Pat. Nos. 4,487,055, 6,026,674, 6,167,746, and/or 7,204,335. A fuel cell sensor is an electrochemical device in which alcohol undergoes a chemical oxidation reaction at a catalytic electrode surface (platinum) to generate an electric current. This current is then measured and converted to an alcohol equivalent reading. Although fuel cell technology is not as accurate or reliable as infrared spectroscopy technology used in evidentiary breathalyzers, they are less expensive and specifically tailored to quantify ethyl alcohol (drinking alcohol). Among manufacturers of IIDs are Smart Start Inc., LifeSafer Interlock, SOS, Ignition Interlock Systems, Intoxalock and Monitech. A list of federally-approved IID devices is maintained by the National Highway Traffic Safety Administration ("NHTSA") in its NHTSA Conforming Products List.

Typically, in order to start a vehicle equipped with an IID, the driver must first blow into the breath analyzer installed in the vehicle or machinery. Conventional IIDs measure the alcohol content of the breath and calculate BAC readings on the alcohol content of gas present in the alveoli of the lungs by approximating, through the use of software algorithms, the alcohol content in the bloodstream. If the driver's BAC exceeds a preset limit, the vehicle's ignition is disabled and the vehicle is rendered inoperable. If the driver's BAC is below the preset limit, ignition is permitted and the vehicle may be started. Exemplary ignition interlock devices that utilize breath analyzers are described in, for example, U.S. Pat. Nos. 3,780,311, 3,824,537, 3,831,707, 4,592,443, and 4,697,666.

Unfortunately, individuals required to use IIDs have become increasingly sophisticated in attempting to trick the device to register false negatives and, in turn, to allow them to drive intoxicated. For example, individuals have been known to have a sober passenger blow into the device and/or use bogus gas samples from balloons or bicycle pumps. Accordingly, the IIDs have become increasingly sophisticated in ensuring that the person providing a breath sample is the person operating the vehicle or machinery. Routinely, IIDs will require a negative pressure (sucking), a positive pressure (blowing), a series of blowing and/or sucking by the operator, and/or retesting while operating the equipment or vehicle. Another deterrent is the Random Rolling Retest. These are random times when the operator is required to provide additional breath samples. This prevents Drinking while driving. Another reason for this is to ensure that an individual cannot have another person provide the first sample to get the car started and then drive home without that person. Most Manufactures set them from within the first 5 to 15 minutes then every 30 to 60 minutes.

Similarly, some of the more onerous IIDs require secondary testing and verification of identity by the operator. For example, along with a breath sample analysis, U.S. Pat. No. 4,158,198 discloses an IID, which incorporates an evaluation of the actual driving by way of a "steady control task" for a designated period of time; U.S. Pat. No. 4,645,939 discloses an IID, which incorporates an evaluation of reflexes using a sequence of time intervals; U.S. Pat. No. 4,723,625 discloses an IID, which incorporates an evaluation of reflexes using a series of test buttons; U.S. Pat. No. 4,738,333 discloses an IID, which incorporates an evaluation of physical tasks, to confirm identity of the driver; and U.S. Pat. No. 6,748,792 and/or United States Patent Publication No. 20070144812 discloses IIDs, which incorporate video cameras to photograph the person giving a breath sample.

While the internal hardware and the function of these monitoring devices are well known in the art, the software used to run, maintain, and report BAC results to the courts and government agencies is not well known. This is due to the fact that the software is typically maintained under trade secret either by the manufacturers of the monitoring device or the companies that service the monitoring devices. To solve this lack of transparency into the software algorithms and computation, the National Highway Traffic Safety Administration (NHTSA) developed model specifications for breath alcohol monitoring devices, which were passed into federal law in 1992, as published in the Federal Register, Vol. 57, No. 67, Apr. 7, 1992, pp. 11774-11787. These NHTSA standards for monitoring devices have been adopted by most states including.

While these NHTSA standards for monitoring devices require that the monitoring devices operate within certain engineering tolerances, they do not require reporting of false positives, false negatives, device failures, and/or maintenance logs for the installed monitoring device. Accordingly, there is no way for the court, MVD, or any other authorized third party to investigate the operating history of a monitoring device and to validate the reliability of the BAC readings. Currently, the monitoring devices and the monitoring device software algorithms lack transparency and do not allow for an authorized third party to verify and validate tests results.

It is estimated that most common monitoring devices have a rate of failure of between 35 to 6% depending on the manufacture, and maintenance, and that these hardware failures are currently either being disregarded or being reported as a false positive or false negative. The penalty for BAC violations recorded by a client's monitoring device range from monetary fines to probation violations and prison. Clients have a real and vested interest in the accuracy and refutability of recorded violations. Because of the nature of the breath testing methodology the requirement of random rolling retest causes false violations. The "partition ration" or formula used to equate ones breath alcohol level with ones blood alcohol level is to multiply the alcohol reading by 2400. That is to say multiply the reading two thousand four hundred times to achieve the blood equivalent. Because of this breath alcohol is a significant problem. Evidentiary machines used to test BAC require a 15 minute depravation period where the law enforcement officer is required to swear that the defendant at no time prior to the breath test burped, or regurgitated anything in their mouth, as to produce mouth alcohol and provide an invalid breath test. Many drivers eat and or drink as they are driving. Many products that do not contain as their primary ingredients may contain alcohol. Many other item produce alcohol as a byproduct as they decay or heat. An example is that smoothies that are available in the retail environment utilize over ripe bananas because of their high fructose levels. A known bi-product of the fruit ripening process is alcohol. This small amount of alcohol when multiplied by the patrician ration may cause a false violation. Under most current systems this leaves two options. First, the violation gets reported to the authorities and the defendant must try to remember what may have caused the violation. Second, the technician who uploads the data from the handset may review the log with the individual and alter or "correct" the log and the violation, real or unreal, will not be reported. The second option destroys the integrity of the data and evidence as it destroys the evidence chain.

Additionally, the NHTSA standards do not require reporting of time, date, and place of detected BAC violations, nor do the NHTSA standards require that personnel responsible for monitoring the monitoring device hardware and software report the time, date, or place of any changes made to the monitoring device data prior to reporting to the court, MVD or other authorized third party. Due to the lack of reporting requirements under the NHTSA standards, criminal courts have exhibited reluctance in certain cases to admit evidence excusing a reported BAC violation and/or admitting evidence of false positive test results.

Other types of monitoring devices are designed to implement and maintain electronic monitoring (tethers) programs to deal with jail overcrowding, pre/post trial applications, juvenile and truancy candidates, and domestic violence. The monitoring devices may comprise drug detection for inclusion and exclusion; alcohol detection for exclusion; required testing for drug, alcohol, sex, behavior, education compliance; location monitoring of users who may be required to participate in various home detention; and any other type of monitoring scenarios.

Various other types of monitoring devices may comprise a Radio Frequency ("RF") Electronic Monitoring device, a Global Positioning Satellite ("GPS") tracking device, a Personal Data Assistant ("PDA") device, and a Field Verification Unit ("FVU") device. Some manufacturers of these types of monitoring devices may include but are not limited to Sentinal Offender Services, Scram Products, Sober Steering Sensors, Actron Systems, etc.

The RF device may be an electronic monitoring system that monitors participants who require basic house arrest services. The RF device is used to ensure curfew compliance. The RF device may be light and typically does not interfere with program participants' day-to-day normal activities. The RF device may snap-on or otherwise attach to the participant to provide quick and easy installation and removal.

The GPS device is a device that may be present with the participant in a monitoring program. The GPS device allows for customized levels of control from an officer. For example, an officer may control offender movement throughout the community by establishing inclusion and exclusion zones there the participant is and is not allowed to go. The GPS device provides an officer with immediate notification of all zone violations. The GPS device may also include a cell phone device (that may utilize a cell phone GPS system with cell tower location and other software), which allows officers to call and speak with the offender directly at anytime of the day or night. The unit can also be used for domestic violence monitoring, sex offenders and other special situations where traditional monitoring is not suitable.

The PDA Device includes officer handheld wireless PDA device offers full mobility for officers while outside the office environment. Officers can use a Website to access offender information and also use the handheld wireless PDA as a direct voice device to communicate directly with program participants via the participants own GPS unit.

The FVU device is a unit that is present with the user. The FVU, device allows officers to perform "drive-by" verification duties that are needed in most electronic monitoring programs. This allows officers to determine a participant's presence or absence at any location.

SUMMARY OF THE INVENTION

The present invention relates generally to a method for providing secure and transparent cached monitoring device data from at least one monitoring device. Generally, as illustrated in FIG. 1 and in accordance with various exemplary embodiments of the present invention, the present method comprises interfacing a central database with at least one monitoring device, uploading data from the at least one monitoring device to the central database, pairing the data with secured transactional data to provide one or more secure transactional stamp(s), storing the data and the paired secure transactional stamp(s) in the central database, producing a report with the data and the paired transactional stamp, and providing the report to an authorized third party.

Preferably, the collection of data from the monitoring device is completed at a remote location, is then uploaded to a central database, and contemporaneously stamped. Most preferably, in accordance with the various exemplary embodiments of the present invention, contemporaneous with the uploading of the data collected from the monitoring device a transactional stamp comprising the name of personnel, time, and any changes made to the data collected from the monitoring device is generated and attached to the data.

Further, in accordance with the various exemplary embodiments of the present invention, the present invention discloses methods for transactional stamping reviews of the monitoring device data by personnel and/or transactional stamping client input data. Additionally, in accordance with the various exemplary embodiments of the present invention, a secure report, comprising at least one of the following: the data collected from the monitoring device; blood alcohol concentration ("BAC") violations; drug violations, hardware/software failures; personnel review data; client input data; data reports, client location, and all corresponding transactional stamps or report data may be provided to the motor vehicle department ("MVD"), government, and/or any authorized third party.

BRIEF DESCRIPTION OF THE DRAWINGS

A more complete understanding of the present invention may be derived by referring to the detailed description and claims when considered in connection with the following illustrative figures. In the following figures, like reference numbers refer to similar elements and steps throughout the figures:

Elements and steps in the figures are illustrated for simplicity and clarity and have not necessarily been rendered according to any particular sequence. For example, steps that may be performed concurrently or in different order are illustrated in the figures to help to improve understanding of embodiments of the present invention.

DETAILED DESCRIPTION OF EXEMPLARY EMBODIMENTS

The present invention may be described in terms of functional block components and various processing steps. Such functional blocks may be realized by any number of hardware or software components configured to perform the specified functions and achieve the various results. In addition, the present invention may be practiced in conjunction with any number of processing methods, and the system described is merely one exemplary application for the invention. Further, the present invention may employ any number of conventional techniques for monitoring participants or user via monitoring devices, interfacing with databases, uploading data from monitoring devices, pairing and storing data in databases, producing reports, and the like.

Methods and apparatus for a providing secured and transparent cached monitoring device data from a monitoring device according to various aspects of the present invention may operate in conjunction with any suitable manufacturing system or device. Various implementations of the present invention may be applied to any system for providing secured and transparent cached monitoring device data from a monitoring device.

Figure 1:
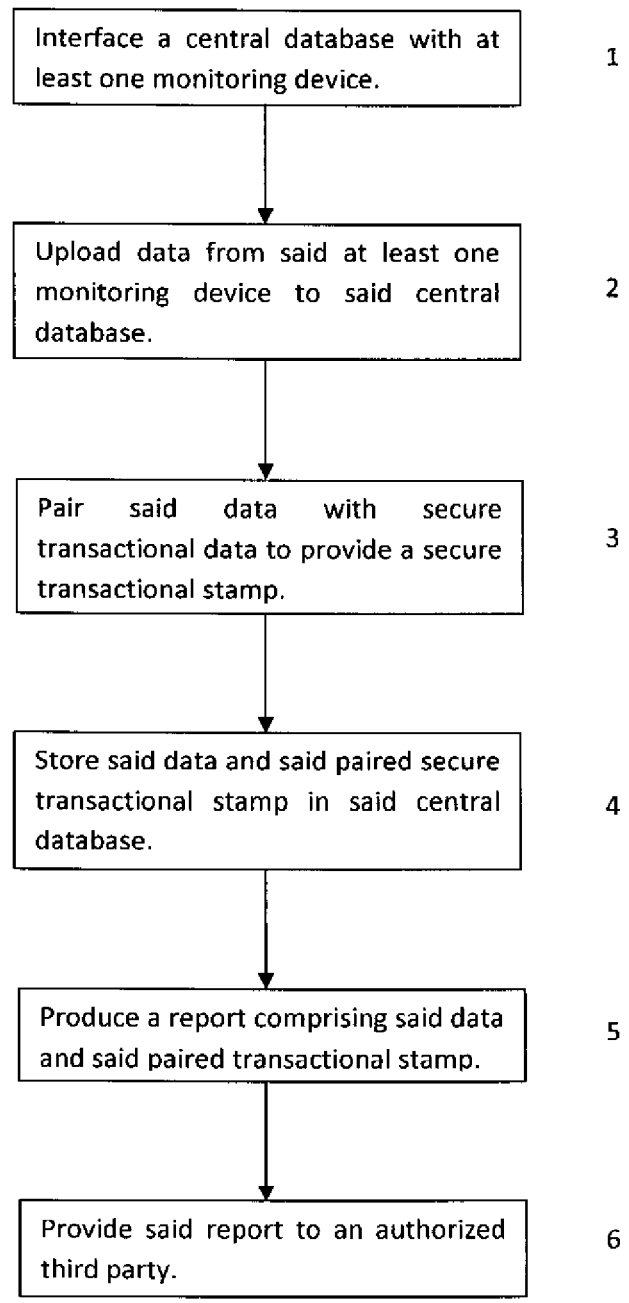
FIG. 1 illustrates a general method for providing secured and transparent cached monitoring device data from a monitoring device in accordance with one exemplary embodiment of the present invention.

Referring now to FIG. 1, a method for providing secured and transparent cached monitoring device data from a monitoring device is described. Generally, as illustrated in FIG. 1 and in accordance with various exemplary embodiments of the present invention, the present method comprises interfacing a central database with a monitoring device 1, uploading data from the monitoring device to a central database 2, pairing the data with secured transactional data to provide a secure transactional stamp 3, storing the data and the paired secure transactional stamp in the central database 4, producing a report with the data and the paired transactional stamp 5, and providing the report to an authorized third party 6.

In accordance with various embodiments of the present invention, the monitoring device may comprise a breath alcohol interlock device ("BIID" or "IID"), a drug detection device, a Radio Frequency ("RF") Electronic Monitoring device, a Global Positioning Satellite ("GPS") tracking device, a Personal Data Assistant ("PDA") device, a Field Verification Unit ("FVU") device, or any other suitable monitoring device.

In accordance with an embodiment of the present invention, the monitoring device may comprise an IID, which may comprise semiconductor sensors, commonly referred to as a Taguchi cell, infrared absorption sensing systems, and/or fuel cells to sense and quantify the amount of alcohol in a driver's breath. Most modern IIDs use an ethanol-specific fuel cell for a sensor. See U.S. Pat. Nos. 4,487,055, 6,026,674, 6,167,746, and/or 7,204,335. A fuel cell sensor is an electrochemical device in which alcohol undergoes a chemical oxidation reaction at a catalytic electrode surface (platinum) to generate an electric current. This current is then measured and converted to an alcohol equivalent reading. Although fuel cell technology is not as accurate or reliable as infrared spectroscopy technology used in evidentiary breathalyzers, they are less expensive and specifically tailored to quantify ethyl alcohol (drinking alcohol). Some manufacturers of IIDs include but are not limited to Draeger Interlock (selling the Draeger Interlock® XT. See www.azsafeharbor.net), Smart Start Inc. (www.smartstartinc.com), LifeSafer Interlock (http://www.lifesafer.com), SOS, Ignition Interlock Systems (See www.aziid.com), Consumer Safety Technology, Inc. (Selling the Intoxalock. See www.arizmat.com), Alcohol Detections Systems, Inc. (Selling The Determinator®. See www.stopdwi.com), Guardian Interlock (Selling the AMS 2000. See www.guardianinterlockaz.com), and Monitech (Selling the QuicTest. See http://www.monitechnc.com/QuicTest1.html). A list of federally-approved IID devices is maintained by the National Highway Traffic Safety Administration ("NHTSA") in its NHTSA Conforming Products List.

One of reasonable skill in the art understands that many new devices are currently being developed and may be developed in the future for sensing, detecting, and quantifying BAC and drug analyses in an individual including sweat sensors and/or percutaneous light sensors. By way of non-limiting example, an IID may include a transdermal BAC reader as disclosed in U.S. Pat. No. 7,413,047 and/or a non-invasive BAC reader and IID as disclosed in U.S. Pat. No. 5,743,349. One of reasonable skill in the art will understand that all of this numerous devices for sensing, detecting, and quantifying BAC and drug analyses are contemplated and disclosed herein.

Generally, the methods for detecting BAC and using ignition interlock systems to prevent automobiles and other machinery from being operated by inebriated individuals are well known in the current art. Moreover, the current invention does not rely on any particular ignition interlock device or method for testing BAC or drug analyses, but instead can be universally applied to any ignition interlock data retrieved from any ignition interlock device installed on any equipment.

In accordance with various embodiments, the monitoring devices may be designed to implement and maintain electronic monitoring (tethers) programs to deal with jail overcrowding, pre/post trial applications, juvenile and truancy candidates, domestic violence, and the like. The monitoring devices may monitor the location of users who are required to participate in various home detention and other types of monitoring scenarios.

In accordance with various embodiment of the present invention, the monitoring devices may comprise a drug detection device, Radio Frequency ("RF") Electronic Monitoring device, a Global Positioning Satellite ("GPS") tracking device, a Personal Data Assistant ("PDA") device, a Field Verification Unit ("FVU") device, and other suitable monitoring device. Some manufacturers of monitoring devices include but are not limited to Sentinal Offender Services, Scram Products, Sober Steering Sensors, Actron Systems, Phone Guard, Logstat Software, etc.

In accordance with various embodiments of the present invention, the drug detection device may comprise or different methodologies of detection similar but not limited to Dräger DrugTest 5000, N-2200 Hand-held Drug Detector, Itemiser® DX, Hardened MobileTrace®, Itemiser® 3 Enhanced, EntryScan®, IONSCAN 400B, IONSCAN 500DT, SABRE 4000, and the like. One of reasonable skill in the art understands that many new drug detection devices are currently being developed and may be developed in the future for drug use of participants. One of reasonable skill in the art will understand that all of these numerous devices for monitoring behavior of participants or users are contemplated and disclosed herein.

In accordance with various embodiments of the present invention, the RF device may comprise an electronic monitoring system that monitors participants or users who require basic house arrest services. The RF device may be used to ensure curfew compliance. The RF device is typically light and does not interfere with program participants' normal day-to-day activities. The RF device may utilize any suitable snap-on technology for quick, easy installation and removal.

In accordance with various embodiments of the present invention, the GPS device may comprise a device that is present with the participant in a monitoring program. The GPS device may allow for customized levels of control from an officer. For example, an officer can control participant movement throughout the community by establishing inclusion and exclusion zones where the participant is and is not allowed to go. The GPS device may provide an officer with immediate notification of any zone violation. The GPS device may comprise a cell phone or PDA device that allows officers to call and speak with the offender directly at anytime of the day or night. The GPS device may also be used for domestic violence monitoring, sex offenders and other special situations where traditional monitoring is not suitable.

In accordance with various embodiment of the present invention, the FVU device comprises a unit that is present with the user. The FVU device may allow officers to perform "drive-by" verification duties that are needed in most electronic monitoring programs. This allows officers to determine a participant's presence or absence at any location.

One of reasonable skill in the art understands that many new monitoring devices are currently being developed and may be developed in the future for monitoring behavior of participants or users. One of reasonable skill in the art will understand that all of this numerous devices for monitoring behavior of participants or users are contemplated and disclosed herein.

Generally, the monitoring devices for monitoring behavior of participants or users are well known in the current art. Moreover, the current invention does not rely on any particular monitoring device or method for monitoring behavior of participants or users, but instead can be universally applied to any monitoring device data retrieved from any monitoring device installed on any equipment.

As illustrated in FIG. 1 and in accordance with various embodiments of the present invention, the central database may be interfaced with at least one monitoring device 1 via at least one wireless connection, and/or at least one wired connections. In accordance with the various exemplary embodiments of the present invention, the central database is interfaced with at least one monitoring device via a wired connection comprising at least one of a USB connection, an Ethernet connection, a DIN connection, a DVI connection, a VGA connection, a DB13W3 connection, and a D-Terminal connection.

Alternatively, as illustrated in FIG. 1 and in accordance with various embodiments of the present invention, the central database may be interfaced with at least one monitoring device via one or more wireless connections comprising at least one wireless access network connection. In accordance with the various exemplary embodiments of the present invention, the central database is interfaced with at least one monitoring device via a wireless connection comprising at least one of a cellular network, microwave, satellite, or any other suitable wireless connection.

As illustrated in FIG. 1 and in accordance with various embodiments of the present invention, after interfacing at least one central database with any number of monitoring devices via any means known to a person of reasonable skill in the art, data is uploaded from the monitoring device(s) to the central database 2. In accordance with the various exemplary embodiments of the present invention, the data collected from the monitoring device(s) may comprise blood alcohol concentration (BAC) or drug analyses test results, diagnostic information of the at least one ignition interlock device, warnings of hardware failures of the monitoring device, speed of vehicle, location of the vehicle, GPS position of the vehicle or person, automotive information, such as, direction of travel, seat belt wearing data, airbag deployment, etc., or any other information contained in the "Black Box" blinker on or off braking etc. or information concerning the verification of the operator's identity.

As illustrated in FIG. 1 and in accordance with various embodiments of the present invention, after uploading data from at least one monitoring device to at least one central database, the data is paired with secured transactional data to provide a secure transactional stamp 3. In accordance with the various exemplary embodiments of the present invention, the secured transactional data may comprise at least one of a time data denoting the time at which the data was collected, a date data denoting the date at which the data was collected, an operator data denoting the name of the operator who uploaded the data from the monitoring device, and a programming data describing any programming changes to the data uploaded from the at least one ignition interlock device.

In accordance with various embodiments of the present invention, the secure transactional stamp may comprise at least one of a time stamp denoting the time at which the data was collected, a date stamp denoting the date at which the data was collected, an operator stamp denoting the name of the operator who uploaded that data from the monitoring device, and a programming stamp describing any programming changes to the data uploaded from the monitoring device.

As illustrated in FIG. 1 and in accordance with various embodiments of the present invention, after creating a secure transactional stamp by pairing the data from at least one monitoring device with the secured transactional data, both the data and the paired secure transactional stamp in are stored in the central database 4. In accordance with the various exemplary embodiments of the present invention, the data and the paired secure transactional stamp in are stored in the central database and are subject to security protocols to ensure chain of custody of the information and to foreclose tampering with either the monitoring device data or the paired secure transactional stamp. In accordance with various embodiments of the present invention, the central database may comprise a secured computer server.

As illustrated in FIG. 1 and in accordance with various embodiments of the present invention, after storing both the data and the secure transactional stamp, a secure report may be produced that catalogues both the data and any paired secure transactional stamp 5. In accordance with various embodiments of the present invention, the secure report may be compiled in any formatting and in any manner suitable to show both the monitoring device data and the corresponding secure transactional stamp.

In accordance with various embodiments of the present invention, the secure report evidences an evidentiary chain of custody in authenticating evidence as required under the Federal Rules of Evidence including, but not limited to Rule 901(a) and Rule 901(b), namely, Rule 901(b)(9). Similarly, in accordance with various embodiments of the present invention, the secure report evidences an evidentiary chain of custody that is a self-authenticating record kept in the customary course of business under the Federal Rules of Evidence including, but not limited to Rule 803(6), Rule 902, namely, Rule 902(11).

Further, in accordance with various embodiments of the present invention, the secure report may be compiled in any formatting and in any manner suitably configured to ensure chain of custody of the information and to foreclose tampering with either the monitoring device data or the paired secure transactional stamp. One of reasonable skill in the art understands that numerous formats including, but not limited to, spreadsheets, charts, lists, graphs, and the like are contemplated and disclosed herein.

As illustrated in FIG. 1 and in accordance with various embodiments of the present invention, after a secure report comprising both the data and the secure transactional stamp is produced, the secure report may be provided to an authorized third party 5. In accordance with various embodiments of the present invention, the authorized third party 5 may comprise at least one of a member of court personnel, a member of motor vehicle department personnel, and a member of police department personnel. Further, in accordance with various embodiments of the present invention, the authorized third party 5 may comprise any court or administrative personnel in the State of Arizona.

Figure 2:
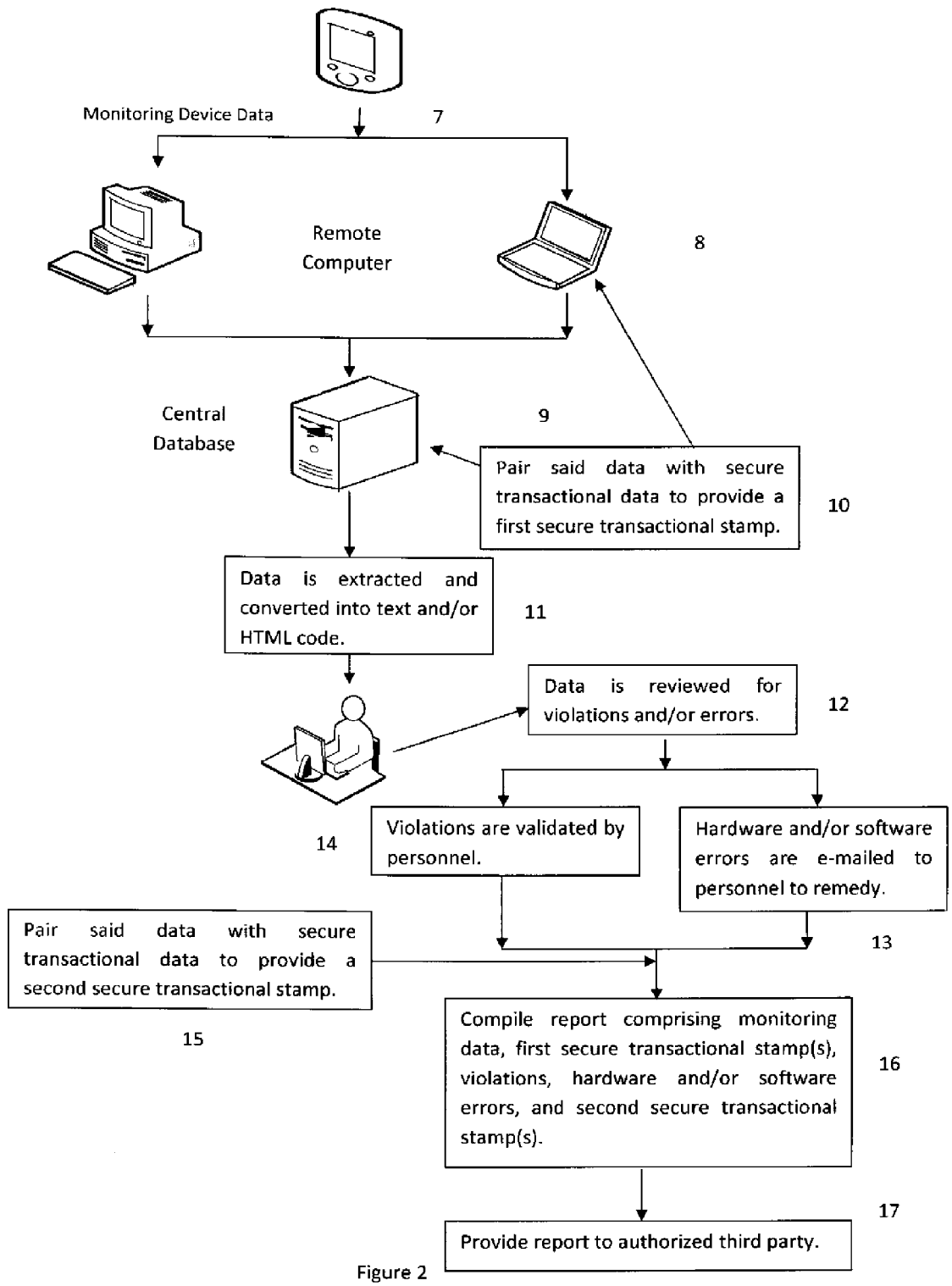
FIG. 2 illustrates a detailed schematic of a method for reporting secured and transparent cached monitoring device data from a monitoring device in accordance with an exemplary embodiment of the present invention.

Generally, as illustrated in FIG. 2, in accordance with various embodiments of the present invention, data is uploaded from at least one monitoring device 7 to a remote computer 8. As illustrated in FIG. 2, in accordance with various embodiments of the present invention, the present method comprises interfacing at least one monitoring device 7 with at least one remote computer 8. In accordance with various embodiments of the present invention, interfacing at least one remote computer 8 with at least one monitoring device 7 by any means discussed above and/or any means known to a person of reasonable skill in the art is contemplated and disclosed herein.

Preferably, in accordance with the various exemplary embodiments of the present invention, the remote or local computer(s) 8 may comprise at least one of a personal digital assistant (PDA) computer, a laptop computer, a desktop computer, a general portable device, such as, and iPad, and the like. In accordance with various embodiments of the present invention, the remote computer(s) 8 may comprise any remote or local electronic storage media known by one of reasonable skill in the art suitable for storing and transferring data.

In accordance with various embodiments of the present invention, using any type, model, or architecture of the monitoring device(s) discussed above and/or any type, model, or architecture of the monitoring device(s) known to a person of reasonable skill in the art is contemplated and disclosed herein.

Similarly, as illustrated in FIG. 2, in accordance with various embodiments of the present invention, any type and sampling rate of the data uploaded from the monitoring device(s) 7 to a remote computer 8 discussed above and/or any typical output data for monitoring device(s) as known by one of reasonable skill in the art is contemplated and disclosed herein.

As illustrated in FIG. 2, after the monitoring device is interfaced: with the remote computer(s) 8 and the monitoring device data 7 is uploaded, the monitoring device data 7 may be paired with secured transactional data to provide a first secure transactional stamp 10. In accordance with the various exemplary embodiments of the present invention, any secured transactional data 10 paired with the uploaded monitoring device data 7 discussed above and/or any secured transactional data 10 known by one of reasonable skill in the art is contemplated and disclosed herein.

As illustrated in FIG. 2, in accordance with various embodiments of the present invention, the monitoring device data 7 and the first secured transactional stamp 10 comprising the paired transactional stamp data may be transmitted from a remote or local computer(s) 8 to a central database 9. FIG. 2 shows that the monitoring device data 7 and the first secured transactional stamp 10 comprising the paired transactional stamp data may be stored and processed in the central database 9. In accordance with various embodiments of the present invention, the monitoring device data 7 and the first secured transactional stamp 10 may be processed, for example, into text and/or html computer code 11. One of reasonable skill in the art will understand that numerous types of computer processing and potential data formats are contemplated and disclosed herein.

As discussed above, in accordance with various embodiments of the present invention, after appropriate processing of the monitoring device data 7, the first secured transactional stamp 10 may be reviewed for violations and software/hardware errors 12, as discussed in detail above. As illustrated in FIG. 2, in accordance with the various exemplary embodiments of the present invention, during the review 12 violations are validated 14 and software and/or hardware errors are e-mailed to service personnel to correct 13. At the conclusion of the review of the monitoring device data 7 and the first secured transactional stamp 10, in accordance with various embodiments of the present invention, service personnel's interaction during the review of the monitoring device data 7 and the first secured transactional stamp 10 may be logged and paired with a second set of secured transactional data 15. One of reasonable skill in the art will understand that processing of monitoring device data, reviewing monitoring device data, and transactional stamping of monitoring device data and review data at the remote or local computer is contemplated and disclosed herein, but it is conceived that a more efficient method of processing, reviewing, and securing transactional data is to complete all functions in a central database/computer.

In accordance with various exemplary embodiments of the present invention, the second set of secured transactional data 15, as with the first set of secured transactional data may comprise at least one of a time data denoting the time at which the review was conducted, a date data denoting the date at which the review was conducted, an operator data denoting the name of the operator who conducted the review, and a programming data describing any programming changes during the review.

As illustrated in FIG. 2, in accordance with various embodiments of the present invention, the second set of secured transactional data 15 creates a second transaction stamp. In accordance with various embodiments of the present invention, this second transaction stamp comprising a second set of secured transactional data 15, along with any additional transaction stamps may be stored in either the remote or local computers 8 and/or the central database 9. One of reasonable skill in the art will understand that numerous sets of reviews may be conducted with numerous paired secured transactional data creating numerous secure transaction stamps. Additionally, one of reasonable skill in the art will understand that the present invention discloses a method to securely log and cache all monitoring device data input into the remote or local computers 8 and/or the central database 9 and to securely log and cache all reviews and/or alterations of the monitoring device data within the remote or local computers and/or the central database.

As discussed above, in accordance with various embodiments of the present invention, multiple, secure transactional stamps preserve monitoring device data creating a credible chain of evidentiary custody is needed and is provided herein. Reliable and validated transparency in recordation of violations, information modification, access by personnel, and client notations constructs a sound basis for the creation of a credible chain of evidentiary custody.

As illustrated in FIG. 2, in accordance with various embodiments of the present invention, after the processing of monitoring device data, reviewing monitoring device data, and transactional stamping of monitoring device data and review data, a secure report may be created comprising at least one of the monitoring device data, the first secure transactional stamp, violations, hardware and/or software errors, the second (and any subsequent) transactional stamp(s) 16. Further, the secure report may be provided to an authorized third party 17. As discussed above, in accordance with various embodiments of the present invention, the authorized third party may comprise any party with requisite authorization to view the report including, but not limited to, a member of court personnel, a member of motor vehicle department personnel, a member of police department personnel in any state, for example, the State of Arizona, or any other suitable candidate which may need the information.

Figure 3:
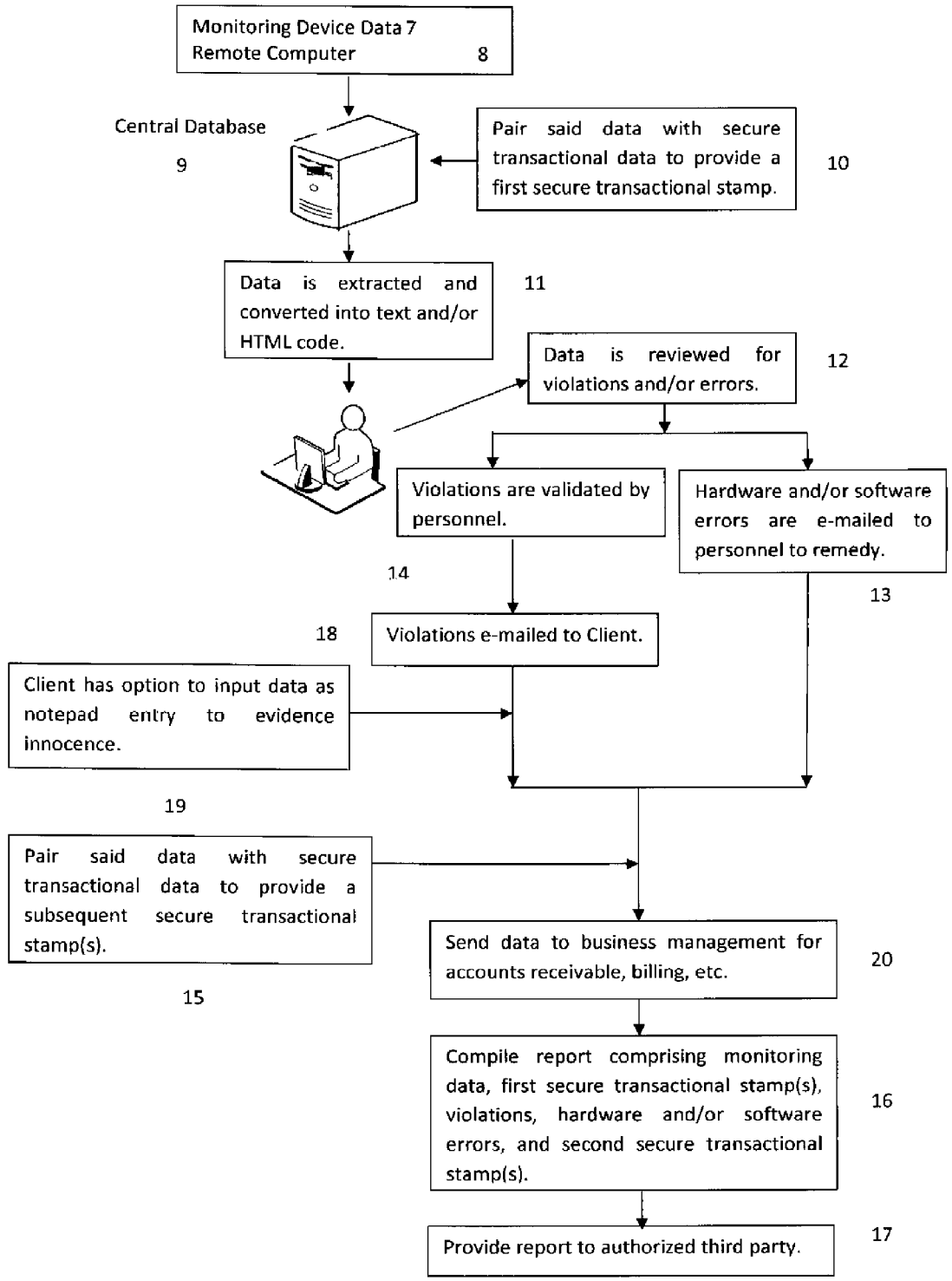
FIG. 3 illustrates a detailed schematic of a method for logging client commentary and business data in connection with secured and transparent cached ignition interlock data from a monitoring device in accordance with an exemplary embodiment of the present invention.

Additionally, in accordance with various embodiments of the present invention, FIG. 3 illustrates a detailed schematic of a method for logging client commentary in connection with secured and transparent cached monitoring device data. As illustrated in FIG. 3 and discussed above, in accordance with various embodiments of the present invention, during the review 12 violations may be validated 14 and, optionally, sent to clients 18. One of reasonable skill in the art will understand that noticing of these violations may be completed via numerous means including, but not limited to, e-mail and/or United States mail and that all of these noticing means are disclosed and contemplated herein.

Further, as illustrated in FIG. 3, in accordance with the various embodiments of the present invention, after a violation is optionally sent to a client 18, the client may enter data into the system as a notepad entry to evidence innocence 19. For example, if a client with a monitoring device takes his car to a restaurant with a valet service, the valet uses the monitoring device to start the vehicle, and the valet registers a violation, then the client may annotate the notepad to describe the event and/or upload data to corroborate the client's story (i.e. upload a copy of the valet ticket). It is apparent to a skilled criminal defense attorney that this corroborating evidence may increase the credibility of the evidence and the chance of a court disregarding the recorded violation.

Likened to the method shown in FIG. 2, FIG. 3 illustrates an exemplary embodiment of the present invention, wherein the subsequent set of secured transactional data 15, similar to the first set of secured transactional data may comprise at least one of time data denoting the time at which the client entered data, date data denoting the date at which the client entered data, and event data describing any events and/or special circumstances entered by the client.

As illustrated in FIG. 3, in accordance with various embodiments of the present invention, the subsequent set of secured transactional data 15 creates a subsequent transaction stamp. In accordance with various embodiments of the present invention, this subsequent transaction stamp comprising a subsequent set of secured transactional data 15, along with any additional transaction stamps, may be stored in either the remote or local computers 8 and/or the central database 9. One of reasonable skill in the art will understand that numerous sets of clients' notes and/or data may be stored with numerous paired secured transactional data creating numerous secure transaction stamps. Additionally, one of reasonable skill in the art will understand that the present invention discloses a method to securely log and cache all IID data input into the remote or local computers 8 and/or the central database 9 and to securely log and cache all client input data within the remote or local computers 8 and/or the central database 9.

Again, as illustrated in FIG. 3, in accordance with the various exemplary embodiments of the present invention, all BAC violations 14, software and/or hardware errors 13, and/or client data input may be sent to business management personnel for accounts receivable, billing, and/or other managerial processing tasks 20.

Figure 4:
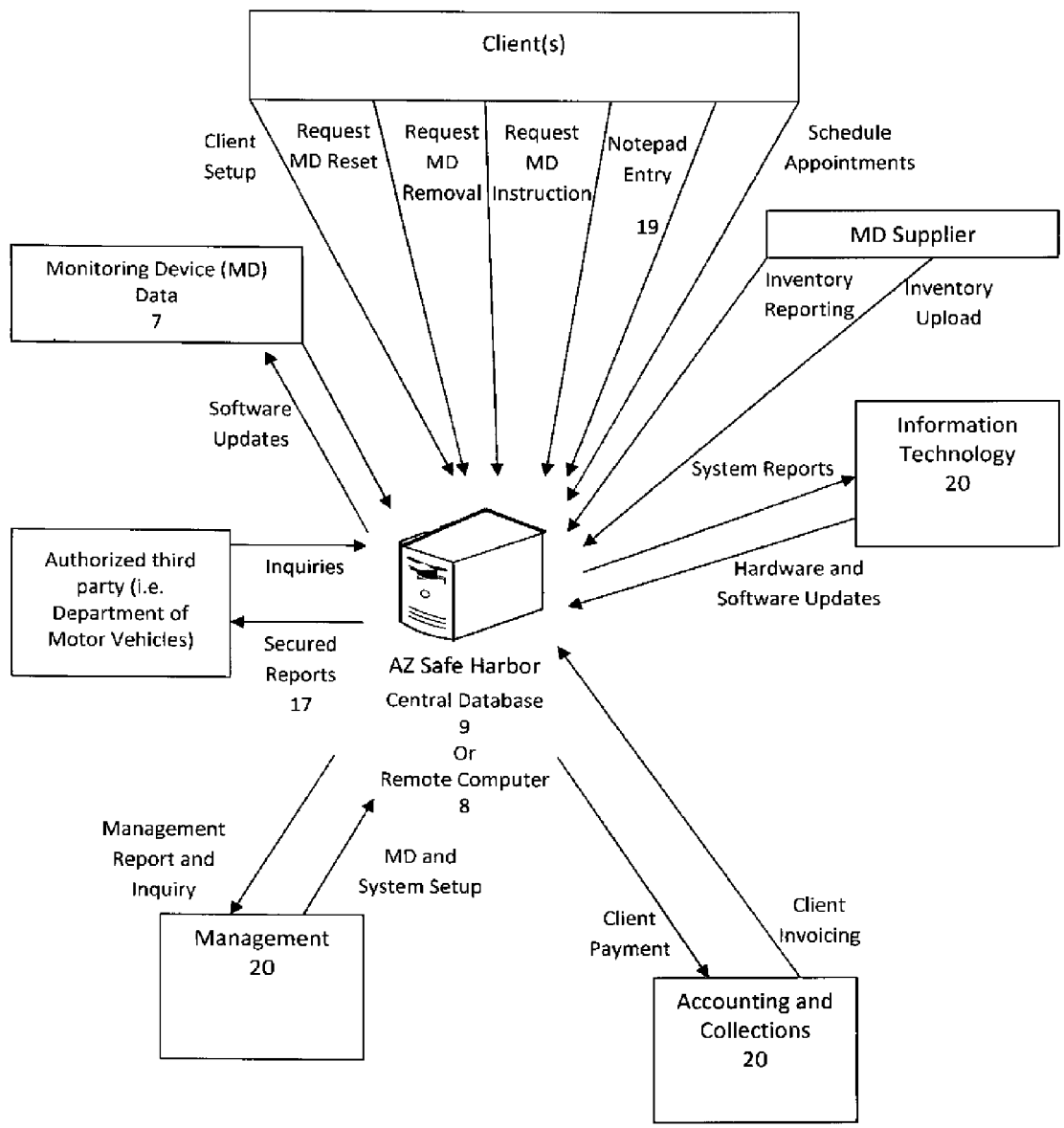
FIG. 4 illustrates a system overview for providing secured and transparent cached monitoring device data from a monitoring device in accordance with an exemplary embodiment of the present invention.

In accordance with various embodiments of the present invention, FIG. 4 illustrates a detailed system overview for providing secured and transparent cached monitoring device data. FIG. 4, in accordance with various embodiments of the present invention, illustrates the interfacing, stamping, storing, processing, reporting, managerial functions, and/or client feedback steps discussed above. In FIG. 4, the monitoring device may be denoted as "MD". Preferably, as shown in FIG. 4, in accordance with the various exemplary embodiments of the present invention, the system may be called "Arizona Safe Harbor," "AZ Safe Harbor," and/or "Safe Harbor."

Figure 5:
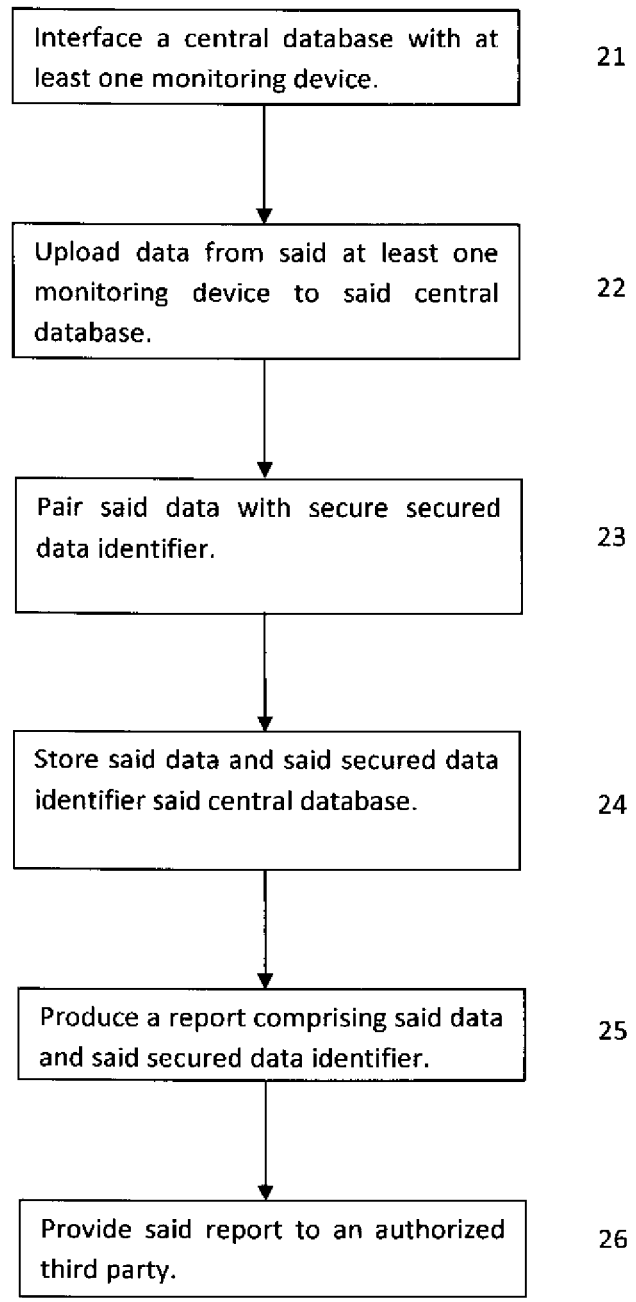
FIG. 5 illustrates a general method for providing secured and transparent cached monitoring device data from a monitoring device in accordance with one exemplary embodiment of the present invention.

As illustrated in FIG. 5 and in accordance with various embodiments of the present invention, the central database may be interfaced with at least one monitoring device 21 via at least one wireless connection and/or at least one wired connection. In accordance with various embodiments of the present invention, the central database is interfaced with at least one monitoring device via a wired connection comprising at least one of a USB connection, an Ethernet connection, a DIN connection, a DVI connection, a VGA connection, a DB13W3 Connection, and a D-Terminal connection.

Alternatively, as illustrated in FIG. 5 and in accordance with various embodiments of the present invention, the central database may be interfaced with at least one monitoring device via one or more wireless connections comprising at least one wireless access network connection.

As illustrated in FIG. 5 and in accordance with various embodiments of the present invention, after interfacing at least one central database with any number of monitoring devices via any means known to a person of reasonable skill in the art, data is uploaded from the monitoring device(s) to the central database 22. In accordance with the various exemplary embodiments of the present invention, the data collected from the monitoring device(s) may comprise blood alcohol concentration (BAC) or drug analyses test results, diagnostic information of the at least one ignition interlock device, warnings of hardware failures of the monitoring device, speed of vehicle, location of the vehicle, GPS position of the vehicle or person, automotive information, such as, direction of travel, seat belts wearing data, airbag deployment, etc. or any other information contained in the "Black Box" blinker on or off braking etc. or information concerning the verification of the operator's identity.

As illustrated in FIG. 5 and in accordance with various embodiments of the present invention, after uploading data from at least one monitoring device to at least one central database, the data is paired with secured data identifier 23. In accordance with various embodiments of the present invention, the secured data identifier may comprise at least one of a time data denoting the time at which the data was collected, a date data denoting the date at which the data was collected, an operator data denoting the name of the operator who uploaded the data from the monitoring device, a programming data describing any programming changes to the data uploaded from the monitoring device.

In accordance with various embodiments of the present invention, the secured data identifier may comprise at least one of a time stamp denoting the time at which the data was collected, a date stamp denoting the date at which the data was collected, an operator stamp denoting the name of the operator who uploaded that data from the monitoring device, a programming stamp describing any programming changes to the data uploaded from the monitoring device, and any other number, symbol, sign, letter, data cell location or any other contemplated data identifier to identify the monitoring data.

As illustrated in FIG. 5 and in accordance with various embodiments of the present invention, after pairing the data from at least one monitoring device with the secured data identifier, both the data and the secured data identifier are stored in the central database 24. In accordance with various embodiments of the present invention, the data and the secured data identifier are stored in the central database and are subject to security protocols to ensure chain of custody of the information and to foreclose tampering with either the monitoring device data or the paired secure transactional stamp. In accordance with various embodiments of the present invention, the central database may comprise a secured computer server.

As illustrated in FIG. 5 and in accordance with various embodiments of the present invention, after storing both the data and the secured data identifier, a secure report may be produced 25 that catalogues both the data and the secured data identifier. In accordance with various embodiments of the present invention, the secure report may be compiled in any formatting and in any manner suitable to show both the monitoring device data and the corresponding secured data identifier.

In accordance with various embodiments of the present invention, the secure report evidences an evidentiary chain of custody in authenticating evidence as required under the Federal Rules of Evidence including, but not limited to Rule 901(a) and Rule 901(b), namely, Rule 901(b)(9). Similarly, in accordance with the various exemplary embodiments of the present invention, the secure report evidences an evidentiary chain of custody that is a self-authenticating record kept in the customary course of business under the Federal Rules of Evidence including, but not limited to Rule 803(6), Rule 902, namely, Rule 902(11).

Further, in accordance with various embodiments of the present invention, the secure report may be compiled in any formatting and in any manner suitably configured to ensure chain of custody of the information and to foreclose tampering with either the monitoring device data or the secured data identifier. One of reasonable skill in the art understands that numerous formats including, but not limited to, spreadsheets, charts, graphs, lists and the like are contemplated and disclosed herein.

As illustrated in FIG. 5 and in accordance with various embodiments of the present invention, after a secure report comprising both the data and the secured data identifier is produced, the secure report may be provided to an authorized third party 26. In accordance with various embodiments of the present invention, the authorized third party may comprise at least one of a member of court personnel, a member of motor vehicle department personnel, and a member of police department personnel. Further, in accordance with the various exemplary embodiments of the present invention, the authorized third party 26 may comprise any court or administrative personnel in any state, for example, the State of Arizona.

Figure 6:
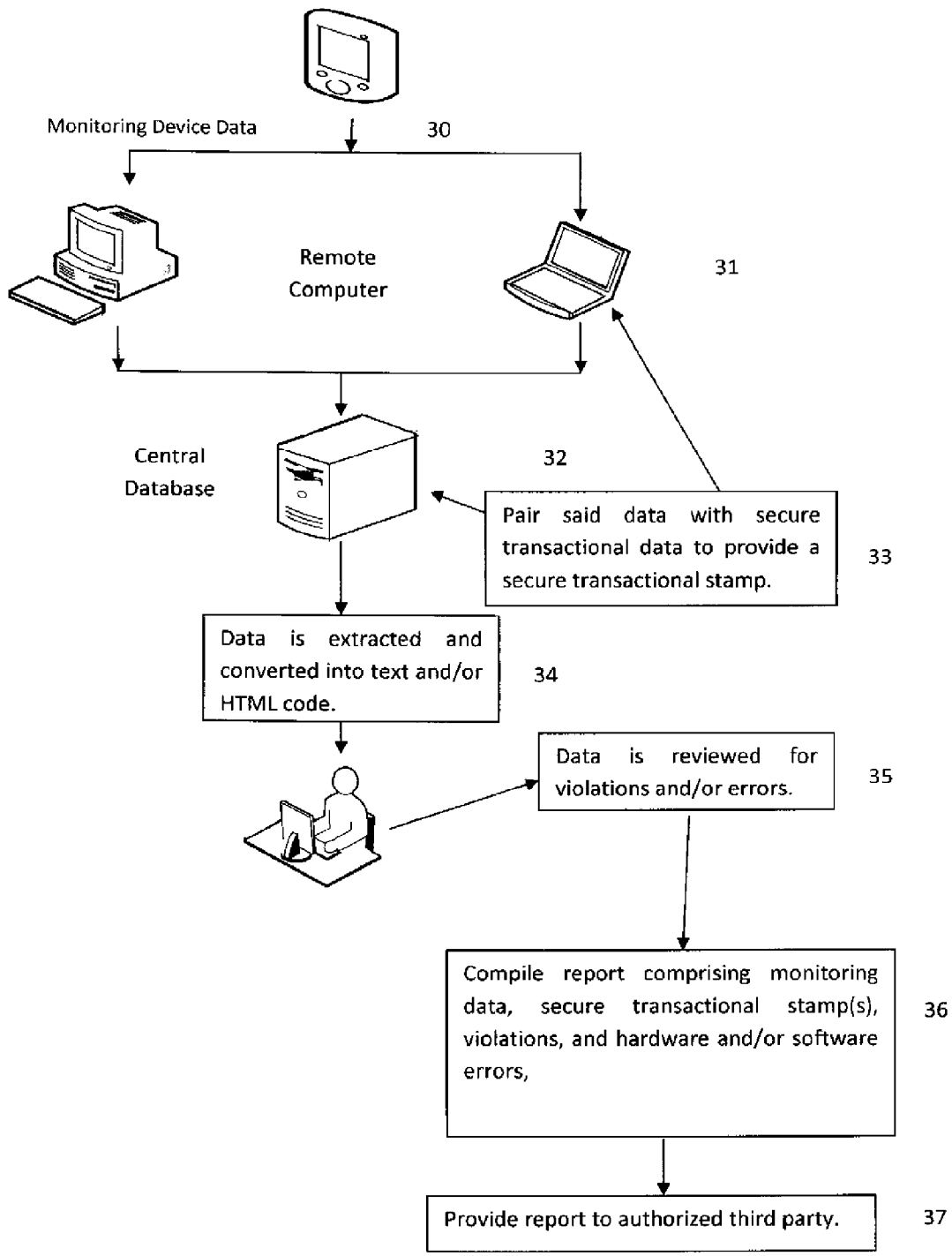
FIG. 6 illustrates a detailed schematic of a method for reporting secured and transparent cached monitoring device data from a monitoring device in accordance with an exemplary embodiment of the present invention.

Similarly, as illustrated in FIG. 6, in accordance with various embodiments of the present invention, any type and sampling rate of the data uploaded from the monitoring device(s) 30 to a remote computer 31 discussed above and/or any typical output data for monitoring device(s) as known by one of reasonable skill in the art is contemplated and disclosed herein.

As illustrated in FIG. 6, after the monitoring device is interfaced with the remote computer(s) 31 and the monitoring device data 30 is uploaded, the monitoring device data 30 may be paired with secured transactional data to provide a secure transactional stamp 33. In accordance with the various exemplary embodiments of the present invention, any secured transactional data paired with the uploaded monitoring device data 30 discussed above and/or any secured transactional data known by one of reasonable skill in the art is contemplated and disclosed herein.

As illustrated in FIG. 6, in accordance with various embodiments of the present invention, the monitoring device data 30 and the secured transactional stamp 33 comprising the paired transactional stamp data may be transmitted from a remote or local computer(s) 31 to a central database 32. FIG. 6 shows that the monitoring device data 30 and the secured transactional stamp 33 comprising the paired transactional stamp data may be stored and processed in the central database 32. In accordance with various embodiments of the present invention, the monitoring device data 30 and the secured transactional stamp 33 may be processed in to text and/or html computer code 34. One of reasonable skill in the art will understand that numerous types of computer processing and potential data formats are contemplated and disclosed herein.

As discussed above, in accordance with various embodiments of the present invention, after appropriate processing of the monitoring device data 30 and the secured transactional stamp 33 may be reviewed for violations and software/hardware errors 35, as discussed in detail above.

As illustrated in FIG. 6, in accordance with various embodiments of the present invention, after the processing of monitoring device data, reviewing monitoring device data, and transactional stamping of monitoring device data and review data, a secure report may be created comprising at least one of the monitoring device data, the secure transactional stamp, violations, hardware and/or software errors 36. Further, the secure report may be provided to an authorized third party 37. As discussed above, in accordance with various embodiments of the present invention, the authorized third party may comprise any party with requisite authorization to view the report including, but not limited to, a member of court personnel, a member of motor vehicle department personnel, a member of police department personnel in the State of Arizona, or any other suitable candidate which may need the information.

These and other embodiments for methods and apparatus for providing secure and transparent cached monitoring data may incorporate concepts, embodiments, and configurations as described with respect to embodiments as described above. The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The invention has been described with reference to specific exemplary embodiments. Various modifications and changes, however, may be made without departing from the scope of the present invention. The description and figures are to be regarded in an illustrative manner, rather than a restrictive one and all such modifications are intended to be included within the scope of the present invention. Accordingly, the scope of the invention should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The present invention has been described above with reference to an exemplary embodiment. However, changes and modifications may be made to the exemplary embodiment without departing from the scope of the present invention. These and other changes or modifications are intended to be included within the scope of the present invention, as expressed in the following claims.

What is claimed is:

1. A method for providing secured and transparent cached monitoring device data from a monitoring device comprising:
   interfacing a central database with at least one monitoring device;
   uploading data from the at least one monitoring device to the central database;
   pairing the data with secured transactional data to provide a secure transactional stamp;
   storing the data and the paired secure transactional stamp in the central database;
   producing a report with the data and the paired transactional stamp; and
   providing the report to an authorized third party.

2. The method of claim 1, wherein the at least one monitoring device comprises at least one of an ignition interlock device, a drug detection device, a Radio Frequency Electronic Monitoring device, a Global Positioning Satellite tracking device, a Personal Data Assistant device, a Field Verification Unit device.

3. The method of claim 2, wherein the at least one ignition interlock device comprises at least one of a DRAEGER INTERLOCK® XT device, an Intoxalock device, a LifeSafer Interlock device, a Smart Start's ignition interlock device, an AMS 2000 device, a QuicTest device, a Determinator device, a Taguchi cell, an infrared absorption sensing system, and a fuel cell configured to sense and quantify the amount of alcohol in a client's breath sample.

4. The method of claim 1, wherein the interface between the central database and the at least one monitoring device comprises at least one of a wireless connection and a wired connection.

5. The method of claim 4, wherein the wired connection comprises at least one of USB connection, an Ethernet connection, a DIN connection, a DVI connection, a VGA connection, a DB13W3 connection, and a D-Terminal connection.

6. The method of claim 4, wherein the wireless connection comprises at least one of a wireless access network connection.

7. The method of claim 1, wherein the data uploaded from the at least one monitoring device comprises blood alcohol concentration test results, drug analysis test results, diagnostic information of the at least one monitoring device, warnings of hardware failures of the at least one monitoring device, speed of a vehicle, location of a vehicle, location of a user, and information concerning the verification of the user's identity.

8. The method of claim 1, wherein the secured transactional data comprises at least one of a time data denoting the time at which the data was collected, a date data denoting the date at which the data was collected, an operator data denoting the name of the operator who uploaded the data from the at least one monitoring device, and a programming data describing any programming changes to the data uploaded from the at least one monitoring device.

9. The method of claim 1, wherein the secure transactional stamp comprises at least one of a time stamp denoting the time at which the data was collected, a date stamp denoting the date at which the data was collected, an operator stamp denoting the name of the operator who uploaded the data from the at least one monitoring device, and a programming stamp describing any programming changes to the data uploaded from the at least one monitoring device.

10. The method of claim 1, wherein the central database comprises a computer server.

11. The method of claim 1, wherein the authorized third party comprises at least one of a member of court personnel, a member of motor vehicle department personnel, and a member of police department personnel.

12. A method for providing secured and transparent cached monitoring device data from at least one monitoring device comprising:
    interfacing at least one local computer with the at least one monitoring device;
    uploading data from the at least one monitoring device to the at least one local computer;
    pairing the data with secured transactional data to provide a secure transactional stamp;
    transmitting the data and the paired secure transactional stamp from the at least one local computer to a central database;
    storing the data and the paired secured transactional stamp in the central database;
    reviewing the data and the paired secured transactional stamp for violations and hardware errors;
    producing a report comprising the data, the paired transactional stamp; and
    providing the report to an authorized third party.

13. The method of claim 12, wherein the at least one local computer comprises at least one of a personal digital assistant (PDA) computer, a laptop computer, and a desktop computer.

14. The method of claim 12, wherein the at least one monitoring device comprises at least one of an ignition interlock device, a drug detection device, a Radio Frequency Electronic Monitoring device, a Global Positioning Satellite tracking device, a Personal Data Assistant device, a Field Verification Unit device.

15. The method of claim 14, wherein the at least one ignition interlock device comprising at least one of a DRAEGER INTERLOCK® XT device, an Intoxalock device, a LifeSafer Interlock device, a Smart Start's ignition interlock device, an AMS 2000 device, a QuicTest device, The Determinator device, a Taguchi cell, an infrared absorption sensing system, a fuel cell, and a transdermal sensing system, and a bodily fluid sensing system configured to sense and quantify the amount of alcohol in a client's breath sample.

16. The method of claim 12, wherein the interface between the central database and the at least one monitoring device comprises at least one of a wireless connection and a wired connection.

17. The method of claim 16, wherein the wired connection comprises at least one of a USB connection, an Ethernet connection, a wireless network connection, a MN connection, a DVI connection, a VGA connection, a DB13W3 connection, and a D-Terminal connection.

18. The method of claim 12, wherein the data uploaded from the at least one monitoring device comprises blood alcohol concentration test results, drug analysis test results diagnostic information of the at least one monitoring device, warnings of hardware failures of the at least one monitoring device, location of a vehicle, speed of a vehicle, location of a user, and information concerning the verification of the user's identity.

19. The method of claim 12, wherein the secured transactional data comprises at least one of a time data denoting the time at which the data was collected, a date data denoting the date at which the data was collected, an operator data denoting the name of the operator who uploaded the data from the at least one monitoring device, and a programming data describing any programming changes to the data uploaded from the at least one monitoring device.

20. The method of claim 12, wherein the secure transactional stamp comprises at least one of a time stamp denoting the time at which the data was collected, a date stamp denoting the date at which the data was collected, an operator stamp denoting the name of the operator who uploaded the data from the at least one monitoring device, and a programming stamp describing any programming changes to the data uploaded from the at least one monitoring device.

21. The method of claim 12, wherein the central database comprises a computer server.

22. The method of claim 12, wherein the authorized third party comprises a member of court personnel, a member of motor vehicle department personnel, and a member of police department personnel in the State of Arizona.

23. The method of claim 12, wherein the report is admissible under Rule 901(b)(9) of the Federal Rules of Evidence.

24. The method of claim 12, wherein the report is admissible under Rule 902(11) of the Federal Rules of Evidence.

25. A system for providing secured and transparent cached monitoring device data from a monitoring device comprising:
    interfacing a central database with at least one monitoring device;
    uploading data from the at least one monitoring device to the central database;
    pairing the data with secured transactional data to provide a secure transactional stamp;
    storing the data and the paired secure transactional stamp in the central database;
    producing a report with the data and the paired transactional stamp; and
    providing the report to an authorized third party.

26. The system of claim 25, wherein the at least one monitoring device comprises at least one of an ignition interlock device, drug detection device, Radio Frequency Electronic Monitoring device, a Global Positioning Satellite tracking device, a Personal Data Assistant device, a Field Verification Unit device.

27. The system of claim 26, wherein the at least one ignition interlock device comprises at least one of a DRAEGER INTERLOCK® XT device, an Intoxalock device, a LifeSafer Interlock device, a Smart Start's ignition interlock device, an AMS 2000 device, a QuicTest device, a Determinator device, a Taguchi cell, an infrared absorption sensing system, and a fuel cell configured to sense and quantify the amount of alcohol in a client's breath sample.

28. A method for providing secured and transparent cached monitoring device data from a monitoring device comprising:
- interfacing a central database with at least one monitoring device;
- uploading data from the at least one monitoring device to the at central database;
- pairing the data with a secured data identifier;
- storing the data and the secured data identifier in the central database;
- producing a report comprising the data; and
- providing the report to an authorized third party.

29. The method of claim 28, wherein the secured data identifier may comprise at least one of number, symbol, sign, letter, data cell location and data identifier.

30. The method of claim 28, wherein the secured data identifier may comprise at least one of a time stamp denoting the time at which the data was collected, a date stamp denoting the date at which the data was collected, an operator stamp denoting the name of the operator who uploaded that data from the monitoring device, a programming stamp describing any programming changes to the data uploaded from the monitoring device, and any other number, symbol, sign letter or any other contemplated identifier to identify the monitoring data.

31. The method of claim 28, wherein the secured data identifier may comprise at least one of a time data denoting the time at which the data was collected, a date data denoting the date at which the data was collected, an operator data denoting the name of the operator who uploaded the data from the monitoring device, a programming data describing any programming changes to the data uploaded from the monitoring device.

32. The system of claim 28, wherein the at least one monitoring device comprises at least one of an ignition interlock device, a drug detection device, a Radio Frequency Electronic Monitoring device, a Global Positioning Satellite tracking device, a Personal Data Assistant device, a Field Verification Unit device.

33. The system of claim 32, wherein the at least one ignition interlock device comprises at least one of a DRAEGER INTERLOCK® XT device, an Intoxalock device, a LifeSafer Interlock device, a Smart Start's ignition interlock device, an AMS 2000 device, a QuicTest device, a Determinator device, a Taguchi cell, an infrared absorption sensing system, and a fuel cell configured to sense and quantify the amount of alcohol in a client's breath sample.

* * * * *